United States Patent
Thornton

[11] Patent Number: 5,957,829
[45] Date of Patent: Sep. 28, 1999

[54] APPARATUS AND METHOD FOR RADIOTHERAPY USING A RADIOACTIVE SOURCE WIRE HAVING A MAGNETIC INSERT

[75] Inventor: Richard T. Thornton, League City, Tex.

[73] Assignee: Advanced Cardiovascular Systems, Inc., Santa Clara, Calif.

[21] Appl. No.: 08/992,037

[22] Filed: Dec. 17, 1997

[51] Int. Cl.$^6$ .................................................. A61N 5/00
[52] U.S. Cl. .................................................................. 600/3
[58] Field of Search ..................................... 600/1–8, 424, 600/407; 128/899

[56] References Cited

U.S. PATENT DOCUMENTS

| | | | |
|---|---|---|---|
| 4,940,452 | 7/1990 | Rohe et al. | 600/7 |
| 5,084,002 | 1/1992 | Liprie | 600/7 |
| 5,092,834 | 3/1992 | Bradshaw et al. | 600/7 |
| 5,103,395 | 4/1992 | Spako et al. | |
| 5,139,473 | 8/1992 | Bradshaw et al. | 600/3 |
| 5,199,939 | 4/1993 | Dake et al. | 600/3 |
| 5,213,561 | 5/1993 | Weinstein et al. | 600/7 |
| 5,302,168 | 4/1994 | Hess | 600/3 |
| 5,503,613 | 4/1996 | Weinberger | 600/3 |
| 5,616,114 | 4/1997 | Thornton et al. | 600/3 |
| 5,643,171 | 7/1997 | Bradshaw et al. | 600/1 |
| 5,662,580 | 9/1997 | Bradshaw et al. | 600/3 |

FOREIGN PATENT DOCUMENTS

WO 94/25106   11/1994   WIPO .................. A61N 5/00

*Primary Examiner*—Samuel Gilbert
*Attorney, Agent, or Firm*—Sheppard, Mullin, Richter & Hampton LLP; James R. Brueggemann

[57] ABSTRACT

A radiotherapy apparatus is disclosed in which a radioactive-tipped source wire is accurately and precisely positioned within an implantable catheter. Embedded within the source wire, adjacent to its distal tip, is a ferrous ball, and a special magnetic sensor assembly is configured to sense the retraction of the source wire to a predetermined home position by sensing the proximity of the embedded ferrous ball.

19 Claims, 2 Drawing Sheets

APPARATUS AND METHOD FOR RADIOTHERAPY USING A RADIOACTIVE SOURCE WIRE HAVING A MAGNETIC INSERT

BACKGROUND OF THE INVENTION

This invention relates generally to the treatment of selected tissue by inter-vivo radiation, for example to prevent restenosis in a patient's vascular system, and, more particularly, to such treatment using a radioactive-tipped source wire.

Coronary vessel stenosis is commonly treated using percutaneous transluminal coronary angioplasty (PTCA), or balloon angioplasty. Several hundred thousand such procedures are performed annually in the United States, and this is believed to constitute about half of the worldwide number of such procedures. The PTCA procedure is popular, because of its relatively high success rate and its minimal invasiveness as compared with coronary bypass surgery.

However, patients treated by PTCA suffer from a high incidence of restenosis, brought on by injury to the arterial wall during the PTCA procedure. In some patients, the injury initiates a repair response in the form hyperplastic growth of the vascular smooth muscle cells in the traumatized region. This hyperplasia narrows the lumen that was opened by the PTCA procedure and necessitates a repeat PTCA or other procedure, e.g., bypass surgery, with attendant high cost and added patient risk.

Intravascular radiotherapy (IRT) has shown significant promise in the prevention or long-term control of restenosis following a PTCA procedure. It also has shown promise in the prevention or long-term control of stenosis following a cardiovascular graft procedure or other trauma to the vessel wall. Typically, IRT is performed by advancing a flexible, radioguide catheter through the patient's cardiovascular system until the catheter's distal tip is located at or near the vessel region to be treated, e.g., the region previously subjected to the angioplasty procedure. A remote afterloader then advances a treatment catheter in the form of a wire having a radiation source at its tip, i.e., a source wire, through the radioguide catheter until the radiation source reaches the vessel region to be treated. The radiation source is held in this region for a prescribed time duration, calculated to deliver an effective dose of radiation to the vessel region to be treated, after which the source wire is withdrawn back into the afterloader for appropriate shielding.

The source wire typically takes the form of a solid lead formed of a nickel-titanium alloy, having the requisite levels of flexibility, springiness, lubricity, mechanical strength, and shape memory retention. The radiation source typically takes the form of a radioactive isotope such as iridium, embedded within the source wire, at its distal tip.

The radioactive source at the end of the source wire must be handled with extreme care. Even short exposures at close distances can result in radiation injury. It is therefore extremely important that the afterloader, which controls the advancement and retraction of the source wire within the radioguide catheter, be manufactured for high reliability, and that it be configured to controllably position the source wire within the radioguide catheter with extreme accuracy and precision. In the past, the controllers that position the distal tip of the source wire within the radioguide catheter have included special optical or mechanical sensors for sensing when that distal tip is located at a home or reference position within the afterloader.

Although such optical and mechanical sensors have operated generally satisfactorily in detecting the presence of the source wire's distal tip at its reference position within the afterloader, the sensors' performance can degrade over time. This degradation is due, in part, to debris accumulating at the site of the sensor. One source of such debris is the radioguide catheter, itself. As the source wire is cycled into and out of a catheter lumen, a certain amount of catheter material is scraped away, and this material is drawn into the afterloader's drive mechanism. This debris can obscure the view of an optical sensor that senses the presence of the source wire's distal tip, and it can accelerate the wear of a mechanical sensor that senses such presence. As a consequence, the presence of the source wire's distal tip at its reference position cannot necessarily be known with the desired level of accuracy and precision.

It should, therefore, be appreciated that there is a need for an improved intravascular radiotherapy apparatus, and related method, that senses the presence of the source wire's distal tip at its home or reference position within the afterloader, while avoiding performance degradation caused by an accumulation of debris from such sources as the radioguide catheter. The present invention satisfies this need.

SUMMARY OF THE INVENTION

The present invention is embodied in a radiotherapy apparatus, and related method of use, for irradiating a selected portion of a patient lumen such as an artery of the patient's cardiovascular system, while avoiding certain performance degradations prevalent in prior apparatus of this kind. The apparatus includes a catheter sized to be insertable into a patient's lumen, and further includes a source wire sized to be slidably insertable into a lumen of the catheter, the source wire including at or near its distal end, a first segment formed of a material that emits radiation and a second segment formed of a material having relatively high magnetic permeability. Further, an afterloader is configured to controllably position the source wire within the catheter lumen, with the source wire's first segment at a selected location, and to withdraw the source wire from the lumen into a predetermined location within the afterloader. A magnetic sensor, associated with the afterloader, senses the presence of the second segment of the source wire at a predetermined home position within the afterloader.

The first and second segments of the source wire are located adjacent to each other at the source wire's distal end, with either of the two segments located immediately adjacent to the end. The source wire can be formed of a nickel-titanium alloy, and the second segment of the source wire can be formed of a ferromagnetic ball. The magnetic sensor can include a guide for guiding the source wire along a predetermined path, a magnetic field source, means defining a magnetic path extending from one pole of the magnetic field source, across the predetermined path for the source wire, and to the other pole of the magnetic field source, and a Hall effect sensor configured to sense a variation in magnetic flux caused by the presence of the second segment of the source wire in a predetermined position in the source wire's predetermined path. In addition, the magnetic field source can take the form of a permanent magnet mounted on an adjustable mount, to allow adjustment of the magnetic flux being directed through the predetermined path of the source wire.

Other features and advantages of the present invention should become apparent from the following description of the preferred embodiments, taken in conjunction with the accompanying drawings, which disclose, by way of example, the principles of the invention.

DESCRIPTION OF THE PREFERRED EMBODIMENTS

Figure 1:
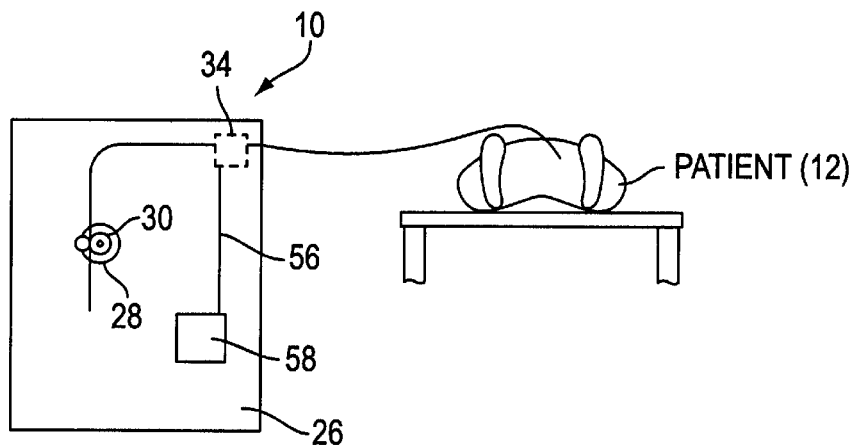
FIG. 1 is a simplified view of an apparatus in accordance with the invention, for use in performing intravascular radiotherapy on a patient, the apparatus incorporating a catheter assembly having a radioactive-tipped source wire.
Figure 2:
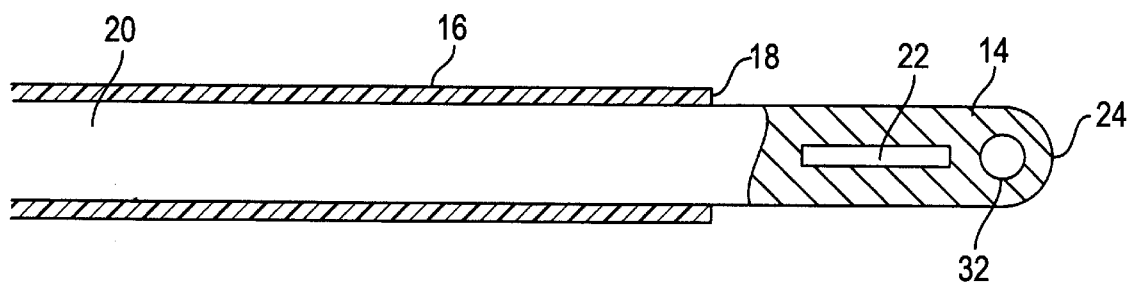
FIG. 2 is a side elevational view, partially in section, of the distal end of a first embodiment of a source wire suitable for use as part of the catheter assembly of FIG. 1, the source wire including a ferrous ball at its distal tip and an iridium core immediately proximal to the ferrous ball.

With reference now to the drawings, and particularly to FIGS. 1 and 2, there is shown an apparatus 10 for performing an intravascular radiotherapy (IRT) procedure on a patient 12, including the controlled delivery of a radioactive-tipped source wire 14 to a region of the patient's vascular system to be treated. IRT has shown significant promise in the prevention or long-term control of restenosis following a percutaneous transluminal coronary angioplasty, or balloon angioplasty, procedure.

To carry out the IRT procedure, a flexible, radioguide catheter 16 is advanced through the patient's cardiovascular system until the catheter's distal tip 18 is located at or near the vessel region to be treated. A lumen 20 extends along the catheter's entire length. The source wire 14, with a radioactive source 22 embedded at or near its distal tip 24, then is controllably advanced through the catheter lumen, until the radioactive source reaches the site of the vessel region to be treated. The source wire remains in this position for a prescribed time duration, calculated to deliver an effective dose of radiation to the vessel region to be treated, after which the source wire is withdrawn fully from the lumen. The lumen's distal end is closed, so that the source wire need not be maintained sterile.

Advancement and withdrawal of the source wire 14 from the lumen 20 of the radioguide catheter 16 is controlled by an afterloader 26. The afterloader includes a reversible stepper motor 28 that is coupled to a drive assembly capstan 30, for controllably advancing and retracting the source wire. Suitable safety interlocks are incorporated within the afterloader to minimize the risk that one or more component failures could cause the source wire's radioactive source 22 to remain within the patient 12 for an excessive time duration, which could lead to significant adverse health consequences, including death. One suitable afterloader is described in detail in U.S. Pat. No. 5,103,395.

It will be appreciated that proper IRT treatment of the patient 12 requires the afterloader 26 to position the source wire 14 and its radioactive source 22 within the patient's cardiovascular system with extreme accuracy and precision. Typically, this has been achieved by configuring the stepper motor 28 and the drive capstan assembly 30 to reliably advance and retract the source wire in precisely repeatable steps, and by accurately sensing the source wire's distal tip 24 when it passes by a prescribed home position within the afterloader. The wire drives an optical encoder 31 that is used for positioning.

The IRT apparatus 10 of FIG. 1 achieves accurate sensing of the source wire's home position by embedding within the source wire's distal end a ferrous metal sphere or ball 32 and by sensing the presence of that ferrous ball at a predetermined position within the afterloader 26 using a magnetic sensor assembly 34. Although a spherical shape is preferred, other three-dimensional shapes could alternatively be used. This magnetic sensor assembly, which preferably incorporates a Hall effect sensor, detects a change in the magnetic flux as the source wire's ferrous ball passes by. The use of magnetic sensing avoids the kinds of performance degradations to which optical and mechanical sensors previously used for this purpose are susceptible.

Figure 3:
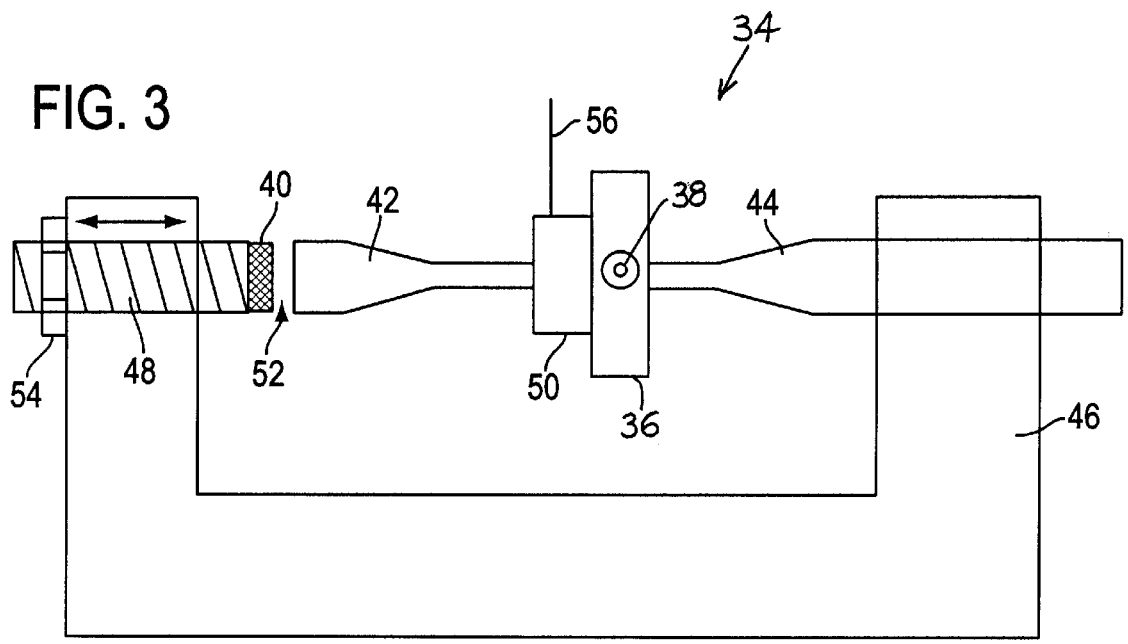
FIG. 3 is a simplified diagram of a magnetic sensor that is part of the apparatus of FIG. 1, for sensing the proximity of the ferrous ball located at the distal end of the source wire portion of the catheter assembly.

More particularly, and with reference to FIGS. 2 and 3 of the drawings, the magnetic sensor assembly 34 includes a guide block 36 that defines a channel 38 sized to receive the source wire 14, and it further includes structure defining a magnetic flux path that extends through the guide block and the source wire channel. This magnetic flux path is defined by a permanent bias magnet 40, two flux directors 42 and 44 mounted on opposite sides of the guide block, and a generally U-shaped support 46. The permanent magnet is mounted on a threaded shank 48 carried at the end of one leg of the U-shaped support. A Hall effect sensor 50 is mounted on the guide block, sandwiched between the guide block and one of the two flux directors. The flux directors, the threaded shank, and the U-shaped support all are formed of a suitable ferrous metal, so that a magnetic path of high permeability is formed from one pole of the magnet to the other, through the guide block and the source wire channel. In an alternative embodiment (not shown in the drawings), the permanent magnet 40 could be substituted by an electromagnet in the form of a wire wound around a portion of the U-shaped support.

The position of the shank 48 on the U-shaped support 46 is threadedly adjustable, so that the size of a small gap 52 between the permanent magnet 40 and the adjacent flux director 42 can be controllably adjusted. A lock nut 54 secures the threaded shank in place. This configuration allows for adjustment of the flux level through the source wire channel 38 in the guide block 36, for optimum detection by the Hall effect sensor 50 of the source wire's ferrous ball 32.

In operation, when the ferrous ball 32 embedded in the source wire 14 passes through the channel 38 of the guide block 36, the Hall effect sensor 50 detects an increased magnetic coupling. The sensor thereupon provides an appropriate signal on line 56 to an electronics subsystem 58 (FIG. 1) of the afterloader 26, which is decoded and used to determine the source wire's reference or home position.

Operation of the magnetic sensor assembly 34 provides several advantages not obtainable by optical and mechanical sensors of the kind previously used to sense the presence of the source wire 14 at its home position. First, the sensor assembly need not make mechanical contact with the source wire, so component wear is avoided. Second, any accumulation of nonferrous debris, e.g., dislodged material from the radioguide catheter 16, will have negligible effect on sensor performance. Third, the need for repeated adjustment is avoided, because the performance of the entire assembly remains fixed after it has been initially adjusted. Finally, the assembly provides highly accurate and repeatable sensing of the proximity of the source wire's tip 24, at least as precise as the size of the ferrous ball 32. Electronic detection of the flux peak can improve accuracy and precision even further.

The source wire 14 preferably is formed of a nickel-titanium alloy, which is a nonmagnetic material and which has the requisite levels of flexibility, springiness, lubricity, mechanical strength, and shape memory retention. The radioactive source 22, which is formed of a suitable radioactive material such as iridium, is embedded within the source wire in a conventional fashion. The ferrous ball 32, likewise, is embedded within the source wire in a conventional fashion.

The source wire 14 depicted in FIG. 2 of the drawings positions the ferrous ball 32 immediately adjacent to the source wire's distal tip 24. The radioactive source 22 is located proximal to, and immediately adjacent to, the ferrous ball. One advantage of this configuration is that it guarantees that the magnetic sensor assembly 34 will detect any failure of the source wire in which the radioactive source detaches from the wire's proximal end. This is because the assembly will fail to sense the passing of the ferrous ball after the wire has been fully retracted into the afterloader.

One disadvantage of the source wire configuration of FIG. 2 is that the ferrous ball 32 will shield some of the radiation emitted axially toward the wire's distal tip 24. This shielding ordinarily would not be a problem in the case of intravascular restenosis treatments, but it might be a minor concern in cancer therapy. Another minor disadvantage of the source wire configuration of FIG. 2 in cancer therapy applications is that the presence of the ferrous ball at the wire's distal tip prevents the radioactive source 22 from being placed as close to the distal end of the lumen 20 of the radioguide catheter 16 as otherwise might be possible.

Figure 4:
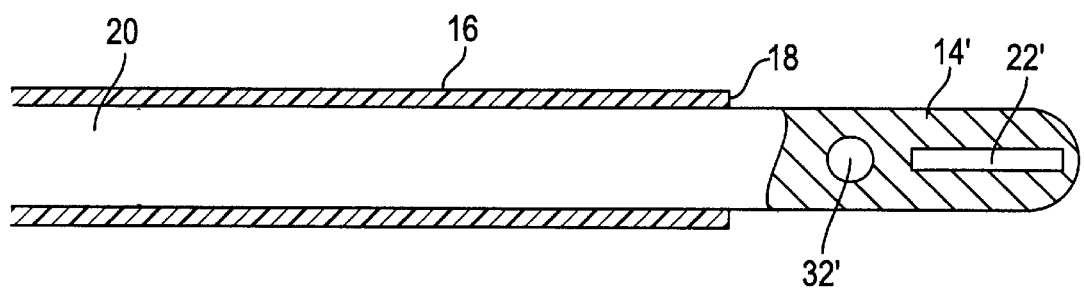
FIG. 4 is a side elevational view, partially in section, of the distal end of a second embodiment of a source wire suitable for use as part of the catheter assembly of FIG. 1, the source wire including an iridium core at its distal tip and a ferrous ball immediately proximal to the iridium core.

FIG. 4 of the drawings depicts an alternative embodiment of a source wire 14' suitable for use in the IRT apparatus 10 of FIG. 1. In this embodiment, the radioactive source 22' is embedded immediately adjacent to the wire's distal tip 24', and the ferrous ball 32' is embedded proximal to the radioactive source. This configuration avoids the shielding and end-closeness disadvantages of the FIG. 2 embodiment, described briefly above. However, it has the disadvantage that the magnetic sensor assembly 34 will be unable to detect a source wire failure in which the radioactive source detaches, but the ferrous ball does not. This disadvantage can readily be overcome, however, by providing an alternate failure detection system, such as a radiation detector within the afterloader 26.

It should be appreciated from the foregoing description that the present invention provides an improved intravascular radiotherapy apparatus that can reliably position a source wire within an implanted radioguide catheter, with reduced susceptibility to degradations caused by any accumulation of debris or the like within the drive mechanism. The apparatus achieves this benefit by embedding a special ferrous ball in the source wire's distal tip and by magnetically sensing the proximity of this ferrous ball when the source wire has been retracted to a predetermined home or reference position.

Although the invention has been described in detail with reference only to the presently preferred embodiments, those skilled in the art will appreciate that various modifications can be made within the scope of the invention. Accordingly, the invention is defined only by the following claims.

I claim:

1. Radiotherapy apparatus for use in irradiating a selected portion of a lumen of a patient, comprising:

a catheter sized to be insertable into a patient lumen, the catheter having a lumen extending along substantially its entire length;

a source wire sized to be slidably insertable into the lumen of the catheter, the source wire including a first segment at or near a distal end thereof, formed of a material that emits radiation, and further including a second segment at or near the distal end thereof, formed of a material having relatively high magnetic permeability;

an afterloader configured to controllably position the source wire within the lumen of the catheter, with the first segment of the source wire at a selected location, and to withdraw the source wire from the lumen of the catheter, into a predetermined location within the afterloader; and a magnetic sensor associated with the afterloader, for sensing the presence of the second segment of the source wire at a predetermined home position within the afterloader.

2. Radiotherapy apparatus as defined in claim 1, wherein the magnetic sensor includes a Hall effect sensor.

3. Radiotherapy apparatus as defined in claim 1, wherein:

the second segment of the source wire is located immediately adjacent to the source wire's distal end; and the first segment of the source wire is located immediately adjacent to, and proximal to, the second segment of the source wire.

4. Radiotherapy apparatus as defined in claim 1, wherein:

the first segment of the source wire is located immediately adjacent to the source wire's distal end; and the second segment of the source wire is located immediately adjacent to, and proximal to, the first segment of the source wire.

5. Radiotherapy apparatus as defined in claim 1, wherein the second segment of the source wire is a generally spherical ball of ferromagnetic material.

6. Radiotherapy apparatus as defined in claim 1, wherein:

the source wire is formed of a nickel-titanium alloy; and the second segment of the source wire is formed of a ferromagnetic material.

7. Radiotherapy apparatus as defined in claim 1, wherein the magnetic sensor includes:

a guide for guiding the source wire along a predetermined path;

a magnetic field source having two poles;

means defining a magnetic path extending from one pole of the magnetic field source, across the predetermined path for the source wire, and to the other pole of the magnetic field source; and a Hall effect sensor configured to sense a variation in magnetic flux caused by the presence of the second segment of the source wire in a predetermined position in the source wire's predetermined path.

8. Radiotherapy apparatus as defined in claim 7, wherein the magnetic sensor further includes an adjustable mount, configured to allow adjustment of the magnetic flux being directed through the predetermined path of the source wire.

9. Radiotherapy apparatus as defined in claim 8, wherein:

the magnetic field source is a permanent magnet; and the permanent magnet is mounted on the adjustable mount.

10. A radiation source wire suitable for use in combination with a catheter insertable into a lumen of a patient, the catheter having a lumen extending along substantially its entire length, the radiation source wire comprising:

an elongated wire sized and configured to be insertable into the lumen of the catheter, the wire being formed of a nonmagnetic material;

a source of radiation located at or near a distal end of the elongated wire; and a magnetic material located at or near the distal end of the elongated wire, adjacent to the source of radiation, wherein proximity of the magnetic material can be sensed, to provide an indication of the position of the source wire within the lumen of the catheter.

11. A radiation source wire as defined in claim 10, wherein:

the source of radiation is located immediately adjacent to the source wire's distal end; and the magnetic material is located immediately adjacent to, and proximal to, the source of radiation.

12. A radiation source wire as defined in claim 10, wherein:

the magnetic material is located immediately adjacent to the source wire's distal end; and the source of radiation is located immediately adjacent to, and proximal to, the magnetic material.

13. A radiation source wire as defined in claim 10, wherein the magnetic material has a generally spherical shape.

14. A radiation source wire as defined in claim 10, wherein:

the wire is formed of a nickel-titanium alloy; and the magnetic material is ferromagnetic.

15. A method for irradiating a prescribed region of a lumen of a patient, comprising:

inserting a catheter into the patient lumen, the catheter having a lumen extending along substantially its entire length;

providing a nonmagnetic source wire that carries a source of radiation at or near its distal tip and that further carries a magnetic material at or near its distal tip, adjacent to the source of radiation; and controllably inserting the source wire to a prescribed position within the lumen of the catheter, wherein controllably inserting includes sensing the presence of the source wire at a predetermined home position using a magnetic sensor sensitive to the magnetic material carried at or near the source wire's distal tip.

16. A method as defined in claim 15, wherein the source wire provided in the element of providing carries the source of radiation immediately adjacent to the source wire's distal end and carries the magnetic material immediately adjacent to, and proximal to, the source of radiation.

17. A method as defined in claim 15, wherein the source wire provided in the element of providing carries the magnetic material immediately adjacent to the source wire's distal end and carries the source of radiation immediately adjacent to, and proximal to, the magnetic material.

18. A method as defined in claim 15, wherein the magnetic material carried by the source wire provided in the element of providing is a generally spherical ball of ferromagnetic material.

19. A method as defined in claim 15, wherein:

the source wire provided in the element of providing is formed of a nickel-titanium alloy; and the magnetic material carried by the source wire provided in the element of providing is of a ferromagnetic material.

* * * * *

UNITED STATES PATENT AND TRADEMARK OFFICE
CERTIFICATE OF CORRECTION

PATENT NO.    : 5,957,829
DATED         : September 28, 1999
INVENTOR(S)   : Thornton It is certified that error appears in the above-identified patent and that said Letters Patent is hereby corrected as shown below:

Title page,
Item [74], *Attorney, Agent or Firm*, please delete "Sheppard, Mullin, Richter & Hampton LLP; James R. Brueggemann" and insert -- Blakely Sokoloff Taylor and Zafman --.

Signed and Sealed this

Eighteenth Day of November, 2003

JAMES E. ROGAN
*Director of the United States Patent and Trademark Office*